(12) United States Patent
White et al.

(10) Patent No.: US 9,888,842 B2
(45) Date of Patent: Feb. 13, 2018

(54) MEDICAL DIAGNOSTIC GAZE TRACKER

(75) Inventors: Sean M. White, Sunnyvale, CA (US); David H. Nguyen, Sunnyvale, CA (US); Kent M. Lyons, Santa Clara, CA (US); Daniel L. Ashbrook, Sunnyvale, CA (US)

(73) Assignee: Nokia Technologies Oy, Espoo (FI)

( * ) Notice: Subject to any disclaimer, the term of this patent is extended or adjusted under 35 U.S.C. 154(b) by 672 days.

(21) Appl. No.: 13/484,442

(22) Filed: May 31, 2012

(65) Prior Publication Data

US 2013/0321772 A1 Dec. 5, 2013

(51) Int. Cl.
*A61B 3/113* (2006.01)
*G06K 9/00* (2006.01)

(52) U.S. Cl.
CPC .......... *A61B 3/113* (2013.01); *G06K 9/00604* (2013.01)

(58) Field of Classification Search
CPC ......... G06F 3/013; A61B 3/113; A61B 3/145; A61B 5/16; G06K 9/00604
USPC .................................. 351/209, 210; 600/558
See application file for complete search history.

(56) References Cited

U.S. PATENT DOCUMENTS

| 5,583,795 | A | 12/1996 | Smyth | 364/516.444 |
| 6,120,461 | A | 9/2000 | Smyth | 600/558 |
| 2010/0039618 | A1 | 2/2010 | DeLemos | 351/209 |
| 2010/0094161 | A1 | 4/2010 | Kiderman et al. | 600/558 |
| 2010/0174586 | A1* | 7/2010 | Berg et al. | 705/10 |
| 2010/0195051 | A1* | 8/2010 | Murray et al. | 351/209 |
| 2011/0043759 | A1* | 2/2011 | Bushinsky | 351/210 |
| 2011/0161076 | A1* | 6/2011 | Davis et al. | 704/231 |
| 2011/0170067 | A1 | 7/2011 | Sato et al. | 351/209 |

FOREIGN PATENT DOCUMENTS

| WO | WO-01/74236 A1 | 10/2001 |
| WO | WO-2008/037299 A1 | 4/2008 |

OTHER PUBLICATIONS

"Construction of the Measurement System and its Experimental Study for Diagnosing Cerebral Functional Disorders Using Eye-Sensing HMD", H. Ishii, et al., 2002, 6 pgs.
"An eye behavior measuring device for VR system", Chern-Shen Lin, Optics and Lasers in Engineering 38, 2002, pp. 333,359.
"Wearable EOG goggles: Seamless sensing and context-awareness in everyday environments", Andreas Bulling, et al., 2009, 15 pgs.
"Real-time Non-Invasive Eyetracking and Gaze-point Determination for Human-Computer Interaction and Biomedicine", Ashlt Talukder, et al., 2004, 9 pgs.

(Continued)

*Primary Examiner* — Marin Pichler
(74) *Attorney, Agent, or Firm* — Harrington & Smith

(57) ABSTRACT

A method to track a user's gaze for medical diagnostics is described. The method includes detecting a gaze behavior of a user in response to a stimulus. The stimulus is a non-diagnostic stimulus. The method also includes determining a type of the stimulus and generating an indication of the gaze behavior and the type of the stimulus. The indication may then be used to generate an expected gaze pattern describing expected gaze behavior to given stimuli. Additionally, the indication may be used to determine whether the gaze behavior is indicative of a potential problem and, in response, an alert may be generated. Apparatus and computer readable media are also described.

20 Claims, 3 Drawing Sheets

(56) References Cited

OTHER PUBLICATIONS

"Neuro Kinetics: Monitoring the Eye to Diagnose Diseases and Conditions", Ben Franklin Technology Partners, 2006, 3 pgs.
"Diagnosing Diseases Via Symptoms of Eyes", Tony Eva, 2011, 2 pgs.

* cited by examiner

MEDICAL DIAGNOSTIC GAZE TRACKER

TECHNICAL FIELD

The exemplary and non-limiting embodiments relate generally to gaze tracking systems, methods, devices and computer programs and, more specifically, relate to tracking a user's gaze for medical diagnostics.

BACKGROUND

This section is intended to provide a background or context. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

The following abbreviations that may be found in the specification and/or the drawing figures are defined as follows:

DP data processor
DSP digital signal processors
MEM memory
NED near eye display
PROG program
RF radio frequency Gaze tracking technology monitors the motion of the user's eyes to determine where the user is looking. Characteristics of the user's gaze may be influenced by the user's medical condition. One traditional gaze tracking machine is the visual field analyzer which can be used to detect peripheral blind spots/areas. The visual field analyzer can also detect glaucoma, brain tumors and other eye diseases.

For the purposes of medical diagnostics, patients are subjected to a variety of tests which present artificial stimuli and the patient's gaze response to the artificial stimuli is recorded. However, these tests are restricted to laboratory settings and do not provide a full view of the characteristics of the patient's gaze.

SUMMARY

The below summary section is intended to be merely exemplary and non-limiting.

The foregoing and other problems are overcome, and other advantages are realized, by the use of the exemplary embodiments.

In a first aspect thereof an exemplary embodiment provides a method to track a user's gaze for medical diagnostics. The method includes detecting a gaze behavior of a user in response to a stimulus. The stimulus is a non-diagnostic stimulus. The method also includes determining a type of the stimulus and generating an indication of the gaze behavior and the type of the stimulus. The indication may then be used to generate an expected gaze pattern describing expected gaze behavior to given stimuli. Additionally, the indication may be used to determine whether the gaze behavior is indicative of a potential problem and, in response, an alert may be generated.

In a further aspect thereof an exemplary embodiment provides an apparatus to track a user's gaze for medical diagnostics. The apparatus includes at least one processor and at least one memory storing computer program code. The at least one memory and the computer program code are configured to, with the at least one processor, cause the apparatus to perform actions. The actions include detecting a gaze behavior of a user in response to a stimulus. The stimulus is a non-diagnostic stimulus. The actions also include determining a type of the stimulus and generating an indication of the gaze behavior and the type of the stimulus.

In another aspect thereof an exemplary embodiment provides a computer readable medium to track a user's gaze for medical diagnostics. The computer readable medium is tangibly encoded with a computer program executable by a processor to perform actions. The actions include detecting a gaze behavior of a user in response to a stimulus. The stimulus is a non-diagnostic stimulus. The actions also include determining a type of the stimulus and generating an indication of the gaze behavior and the type of the stimulus.

In a further aspect thereof an exemplary embodiment provides an apparatus to track a user's gaze for medical diagnostics. The apparatus includes means for detecting a gaze behavior of a user in response to a stimulus. The stimulus is a non-diagnostic stimulus. The apparatus also includes means for determining a type of the stimulus and means for generating an indication of the gaze behavior and the type of the stimulus.

BRIEF DESCRIPTION OF THE DRAWINGS

The foregoing and other aspects of exemplary embodiments are made more evident in the following Detailed Description, when read in conjunction with the attached Drawing Figures, wherein.

DETAILED DESCRIPTION

Figure 1:
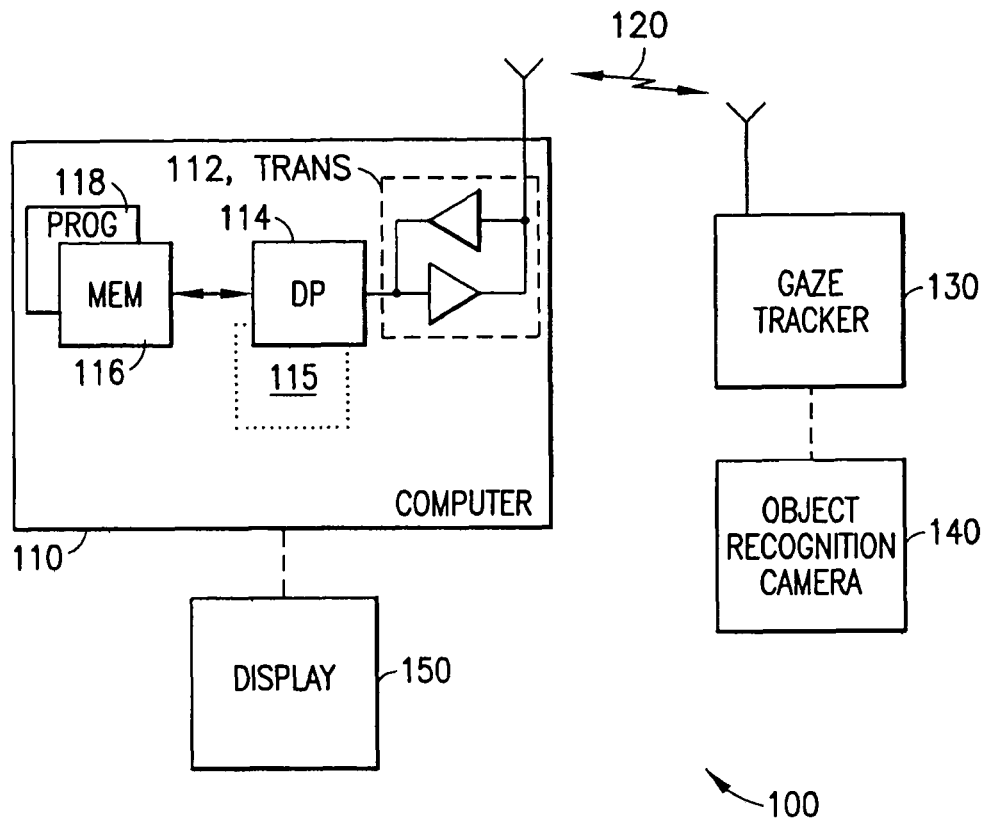
FIG. 1 shows a simplified block diagram of exemplary electronic devices that are suitable for use in practicing various exemplary embodiments.

Reference is made to FIG. 1 for illustrating a simplified block diagram of various electronic devices and apparatus that are suitable for use in practicing exemplary embodiments. In the system 100 of FIG. 1, a computer 110 includes a controller, such as a computer or a data processor (DP) 114 and a computer-readable memory medium embodied as a memory (MEM) 116 that stores a program of computer instructions (PROG) 118. The computer may also include a suitable wireless interface, such as radio frequency (RF) transceiver 112, for bidirectional wireless communications via one or more antennas. Computer 110 may communicate with a display 150 (such as a monitor), for example, to present a viewable screen.

Gaze tracker 130 is configured to observe a gaze of a user and provide data to the computer 110. Gaze tracker 130 is shown as capable of communication with the RF transceiver 112 of the computer. However, as an alternative, gaze tracker 130 may be incorporated as part of either the computer 110 and/or the display 150. In a non-limiting embodiment, the gaze tracker 130 may be operated with an object recognition camera 140 configured to view in the direction of the gaze of the user. The data from the object recognition camera 140 may be used to determine what object or objects the user is observing. The object(s) being viewed by the user may be considered stimulus or stimuli.

Figure 2:
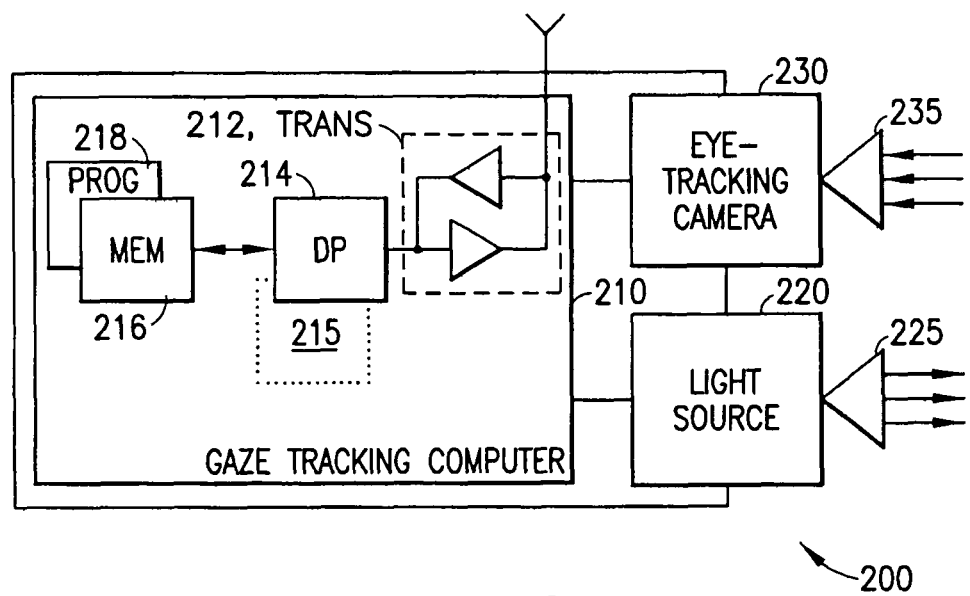
FIG. 2 shows a simplified block diagram of an exemplary gaze tracker that is suitable for use in practicing various exemplary embodiments.

FIG. 2 shows a simplified block diagram of another exemplary gaze tracker 200 that is suitable for use in practicing various exemplary embodiments. In the gaze tracker 200 of FIG. 2, a gaze tracking computer 210 includes a controller, such as a computer or a data processor (DP) 214 and a computer-readable memory medium embodied as a memory (MEM) 216 that stores a program of computer instructions (PROG) 218. The gaze tracker 200 may include of a light source 220 (such as an inferred light) to produce light 225 used to illuminate the eye and provide reflections 235 on the surface of the eye that can be tracked by an eye-tracking camera 230.

The gaze tracker 200 may also include a suitable wireless interface, such as radio frequency (RF) transceiver 212, for bidirectional wireless communications via one or more antennas. The gaze tracker 200 may use the wireless interface in order to communicate with another computer (or network). In a further exemplary embodiment of the gaze tracker 200, the gaze tracker 200 may be connected to a computer via a wired connection (not shown).

The PROGs 118 and 218 may include program instructions that, when executed by the associated DP 114 and DP 218, enables the devices to operate in accordance with exemplary embodiments, as will be discussed below in greater detail. That is, various exemplary embodiments may be implemented at least in part by computer software executable by the DP 114 of the computer 110 and DP 214 of the gaze tracker 200, or by hardware, or by a combination of software and hardware (and firmware). The computer 110 may also include dedicated processors, for example gaze tracking analysis processor 115 and gaze tracking analysis processor 215.

The computer readable MEMs 116 and 216 may be of any type suitable to the local technical environment and may be implemented using any suitable data storage technology, such as semiconductor based memory devices, flash memory, magnetic memory devices and systems, optical memory devices and systems, fixed memory and removable memory. The DPs 114 and 214 may be of any type suitable to the local technical environment, and may include one or more of general purpose computers, special purpose computers, microprocessors, digital signal processors (DSPs) and processors based on a multicore processor architecture, as non-limiting examples. The wireless interfaces (e.g., RF transceivers 112) may be of any type suitable to the local technical environment and may be implemented using any suitable communication technology such as individual transmitters, receivers, transceivers or a combination of such components.

The display 150 may be of any type suitable to the local technical environment. For example, the display 150 may be implemented using any suitable display technology, such as cathode ray tube, LED screens, etc. As a non-limiting example, various exemplary embodiments may use a near eye display (NED) device for gaze tracking. A near eye display provides a graphical display close to the eye or eyes of the user. This is often instantiated in the form of glasses or similar eye wear or head gear.

As used herein, a "gaze behavior" describes how a gaze of a user is acting. As non-limiting examples, the actions of the gaze of a user may be described as fixated (such as on a specific item or area), or reading (such as saccade movements over a line of text) or erratic. The gaze behavior includes a description of the actions of the gaze, for example, by describing a single action and/or by describing a series of action. For example, one type of gaze behavior may comprise the gaze of a user being fixated for a given time and then becoming erratic. As another example, one type of gaze behavior may comprise the gaze of a user reading a line of text followed by immediately or substantially immediately reading the same line of text again.

A gaze behavior may be associated with a certain stimulus or a type of stimulus. For example, the type of stimulus may comprises a face, or text, etc. Thus, a gaze behavior may be associated with a face, or text, etc. A gaze behavior may be associated with a specific stimulus. For example, the specific stimulus may comprise a specific person's face, or a specific page in a book, etc. A gaze behavior and associated stimuli (or type of stimuli) may be referred to as a gaze behavior/stimuli pairing.

An exemplary embodiment may use gaze tracking for the purposes of medical or general physiological diagnostics. In particular, the gaze tracker 130, 230 may be used to track the gaze of the user. "Gaze tracking" is the tracking of a gaze of a user over a period of time. Tracking of the gaze of the user can be used to establish a "gaze behavior" of the user. The gaze behavior may be based on everyday or 'real world' stimulus or stimuli. The stimulus or stimuli is visual information received by the eye(s) of the user (or at least located in front of the user's eye(s), or perhaps at the peripheral view of the user's eye(s)). For example, one type of stimulus may be a book which a user is reading. As another example, one type of stimulus may be images displayed on a television screen or movie screen when the user is watching a movie. As another example, the stimulus may be a face of a person when the user is looking at the face of that person. As another example, the stimulus may be a pattern when the user is looking at that pattern, such as playing a board game or card game for example. The stimulus/stimuli could be any suitable type of information which the user might observe during normal living. The stimulus/stimuli need not be a clinical type of diagnostic stimulus. In one type of example, the "real world" gaze behavior may be recorded.

In one type of example, an individual user's gaze behavior may be compared to a historic gaze pattern(s) or canonical diagnostic gaze pattern(s). Deviations from those historic gaze pattern(s) may be detected. This comparison may be provided on a continuing basis (such as when the user is not in an exam room for example). In one type of example, the comparison and/or deviation may be recorded.

Eye care professionals use a machine called a visual field analyzer for gaze tracking. However, because the visual field analyzer is large and bulky, the visual field analyzer is limited to use during office visits. With features as described herein, a medical diagnostic may be done, similar to what is done with a visual field analyzer, but without having to use the large and bulky visual field analyzer. In one type of example, gaze tracking may be performed during everyday living of the user by using gaze tracking technology through glasses-based (head-mounted display) tracking. As another example, gaze tracking may be performed using gaze tracking technology while the user is working or using a computer monitor. Whereas the visual field analyzer uses a specific stimulus (such as a moving dot) to detect the patient's reaction in terms of eye movement, an exemplary embodiment may use what is already being viewed by the user as normal everyday stimulus/stimuli, such as through the glasses of a user or displayed on a computer monitor.

That is, in contrast to conventional systems that look at reactions to known, virtual stimuli which is provided for diagnostics (for example, alternating images, a moving ball), an exemplary embodiment may observe gaze-based behaviors to non-diagnostic stimuli. The non-diagnostic stimulus/stimuli may comprise real world stimuli and other stimuli not generated specifically for the purposes of diagnostics. As used herein, the term "non-diagnostic stimuli" and "non-diagnostic stimulus" is intended to mean visual stimuli/stimulus which is not specifically created or generated for a diagnostic testing machine/apparatus/method.

An exemplary embodiment provides a system which can be used in several ways. In one example it may compare a historical gaze pattern with current gaze behavior to find differences. A "gaze pattern" may comprise information regarding one or more previous gaze behavior(s) relative to one or more associated stimulus/stimuli, such as real world stimuli for example. When there is a predetermined difference of the gaze behavior relative to the gaze pattern, the system may alert the user, and/or a medical professional, and/or other related person or system. For example, the system may have a gaze pattern for when the user reads a "text" type of stimuli. If a predetermined difference between the gaze pattern and the gaze behavior occurs, the system may be configured to note an anomaly. For example, if a user reads a same line of text or a same paragraph over and over again, such as 10-15 times for example, the system may be configured to perform a predetermined action, such as to note an anomaly for example.

As used herein, a "gaze pattern" describes a gaze behavior(s) which is expected in response to a certain stimuli (or type of stimuli). For example, a "gaze pattern" for reading English language text in a book may comprise the user's gaze moving from left to right, and then relatively quickly from right to left as the user reaches the end of a line and moves to a new line. In addition, the "gaze pattern" may comprise the user's gaze moving down slowly over time as multiple lines of text are read.

In the gaze pattern, an individual stimulus may be associated with one or more gaze behaviors, which indicates that any one of the gaze behaviors are expected as a response to the stimulus. Additionally, multiple stimuli may be associated with the same gaze behavior indicating that the same gaze behavior is expected as a response to any of the stimuli. The gaze pattern may be established based on a historic series of gaze behaviors and associated types of stimuli for a specific individual. Additionally or alternatively, the gaze pattern may be established based on a historic series of gaze behaviors and associated types of stimuli of multiple people (for example, from a large sampling of people).

In one type of example embodiment, the system may have a set of known gaze pattern(s) to real world stimuli that should be noted when observed in the user. For example, a person with dementia, Alzheimer's or a dissociative disorder may stop looking at facial features when encountering other people or may spend an inordinate time looking at facial features trying to identify them. If such an event occurs, the system may be configured to send an alert to the appropriate people.

Another exemplary embodiment may also provide virtual stimuli in augmented reality scenes. An augmented reality scene may include computer generated information displayed with 'real world' images or displayed to overlap real world views. For example, a camera screen may display the image observed by the camera with labels added to provide details of items in the screen (such as buildings, streets, etc.). Alternatively, computer generated information may be provided on a medium (such as on a lens of a pair of glasses) so that the computer generated information is visible when looking through the medium.

In one type of example embodiment, an observed gaze behavior/stimuli pairing may be compared against a gaze pattern. If the observed gaze behavior does not match one of the expected gaze pattern(s) associated with the same stimuli (or type of stimuli) as the observed stimuli, then the observed gaze behavior/stimuli pairing is considered to deviate from the gaze pattern.

Figure 5:
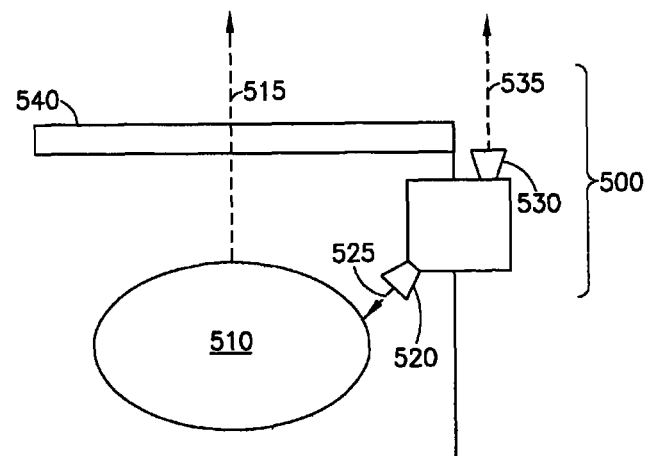
FIG. 5 shows another simplified block diagram of an exemplary headset that is suitable for use in practicing various exemplary embodiments.

In another exemplary embodiment, a headset may be provided includes both a gaze tracker and a camera directed in the direction of the users gaze (such as a front facing camera as shown in FIG. 5, described below). When a gaze behavior is detected, the system may be configured to identify a specific object(s) seen by the user, such as text, photos, faces, etc. The object(s) viewed may be identified using object recognition techniques, for example, but not limited to, optical character recognition (for text), template matching, weak classifier cascades, bag of features, edge-matching, and histogram matching. The objects may then be assigned to a "type" or classification of stimulus (for example, text documents, faces, etc.). The gaze behavior may then be associated with the object (or type of stimulus) being viewed. The headset may then be configured to generate an indication of the gaze behavior and the type of the stimulus. For example, the indication may be by reference to a table of behaviors and to a table of stimulus. This indication can be stored in a log and/or stored in a buffer for transmission as part of a message.

When providing a message, the indication may be included in a notification to the user (for example, as a warning on the display), an alert to a doctor, etc. The message may be formatted as appropriate, for example, formatted as a text message to be sent via SMS, or formatted as an email to be sent via the internet. Additionally, the headset may provide an audio indicator to the user (for example, using a speaker) when such messages are sent.

The headset may be configured to continuously monitor gaze behavior and log events for specific gaze behaviors. The specific gaze behavior may be those that are identified as abnormal. In one type of example, the headset may log events for certain gaze behavior/stimuli pairings, for example, when taking inordinate time looking at facial features.

In another non-limiting example, when a specific gaze behavior is detected, the gaze behavior may be compared against a list of behaviors. The list may provide an indication of one or more actions to be taken. For example, the action may be to log the event, or to send a message to a doctor (or a list of doctors/emergency personal). The list may include specific behavior/stimuli pairings and the associated actions to be taken.

In a further non-limiting example, the gaze behavior may be compared against a gaze pattern. If the gaze behavior deviates from the gaze pattern, then appropriate action(s) may be taken (such as logging the event, sending a message, etc.). The gaze pattern may be developed over a period of time. Alternatively or additionally, the gaze pattern may be provided when the gaze tracking device is set-up.

A gaze tracking device may be used to gather additional information about the user's eye. For example, a gaze tracking device may be configured to determine the size of the user's pupils, to detect corneal arcus (deposits around the eye), and/or to determine the position of the user's eyelid.

A computer may process the data gathered by the gaze tracking device and provide analysis. The computer may highlight that the user exhibits symptoms and identify the possible diagnosis. For example, the computer may note that a user is showing a lack of eye contact during conversations and note that this may be a symptom of ADHD. Similarly, the computer may identify a historic record of a dropping of the user's eyelids as a possible symptom of acute ptosis. Other possible symptoms the computer can track may include, for example: differences in the size of the pupils, differences in the speed of contraction/dilation, occurrence of corneal arcus (a symptom of Wilsons disease), etc.

An exemplary embodiment provides a method for using a near eye display (NED) to diagnosis a medical condition. The NED includes an optical gaze tracker to detect the eyeballs. Since the NED displays images throughout its normal operation, the user's gaze in reaction to those images may then be used for diagnosis. Thus, the NED can perform diagnostic measurements without supplying artificial stimuli. This forms a stimuli and detection feedback loop for the medical diagnosis.

Figure 3:
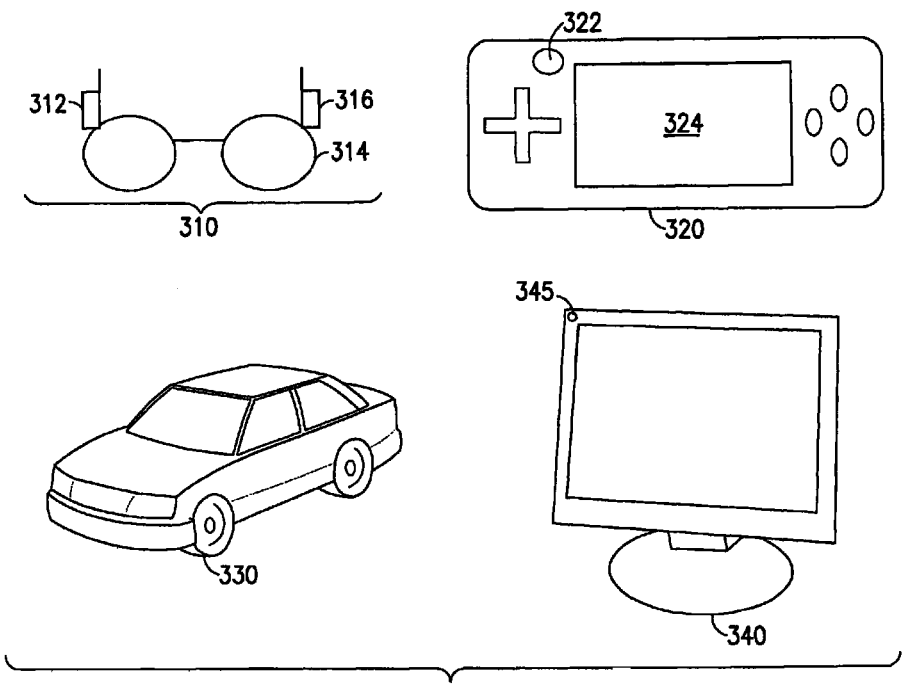
FIG. 3 is an illustration of various devices that may incorporate an exemplary embodiment.

FIG. 3 is an illustration of various devices that may incorporate an exemplary embodiment. As shown, a gaze tracker may be incorporated into a pair of glasses 310 (or headset), a portable gaming device 320, a car 330 (for example, in the dashboard) and a computer monitor 340.

The various devices may include a gaze tracker and may also include a display and/or a forward facing camera. For example, the pair of glasses 310 may include a gaze tracker 312 and display images on one or both lenses 314. The pair of glasses 310 may also include a camera 316 which faces in the direction of the user's gaze. The camera 316 may be used to determine which objects the user is looking at.

As shown, portable gaming device 320 includes a gaze tracker 322 and a display 324. The gaze tracker 322 may be used to determine which images shown on the display 324 the user is observing. Similarly, the computer monitor 340 includes a gaze tracker 345 to determine which images on the computer monitor 340 the user is viewing. The images shown on the display 324 or computer monitor 340 may be categorized by a broad type of image (for example, text document, video of people, etc.) which may (or may not) correlate to the possible types of stimuli.

In the example of a car 330, the gaze tracker may be embedded in the dashboard in order to detect the gaze direction of the user/driver. Images may be displayed on a screen in the dashboard (such as a speedometer) and/or on a heads-up display (HUD) on the windshield. Alternatively, forward facing cameras (such as in the headlights) may be used to determine objects in front of the vehicle which the user/driver is observing.

FIG. 5 shows a simplified block diagram of an exemplary headset 500 that is suitable for use in practicing various exemplary embodiments. The headset 500 includes of a gaze tracker 520 which faces in direction 525 at the user's eye 510. The headset also includes a lens 540 and a forward facing camera 530.

The lens 540 may be used to display images. The gaze tracker 520 may then be used to determine the direction 515 of the user's gaze (also referred to as the gaze direction) and consequentially which image displayed on the lens 540 is being observed. Alternatively (or additionally when the lens is not used to display images), the forward facing camera 530 may be faced (or focused) in direction 535 in order to observe the same view as the user. Direction 535 may be substantially the same as direction 515 (for example, when viewing distant objects) or direction 535 may be corrected to account for the difference in location (for example, when viewing nearby objects).

Figure 6:
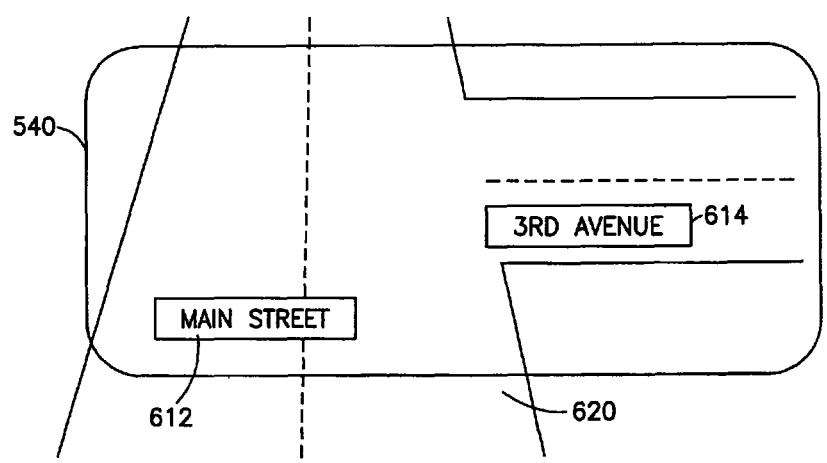
FIG. 6 shows a simplified view through the exemplary headset of FIG. 5.

FIG. 6 shows a simplified view through the lens 540 of headset 500. As shown, the lens 540 is transparent allowing the user to view road 620. Displayed on the lens 540 is information regarding the view, specifically, label 612 which identifies the road 620 the user is on (Main Street) and label 614 which identifies the cross-street (3rd Avenue). As noted above, gaze tracker 520 may be used to determine whether the user is looking at a label (612, 614). When not looking at a label, forward facing camera 530 may then be used to determine which object the user is viewing, such as the road 620.

Based on the foregoing it should be apparent that various exemplary embodiments provide a method, apparatus and computer program(s) to track a user's gaze for medical diagnostics.

Figure 4:
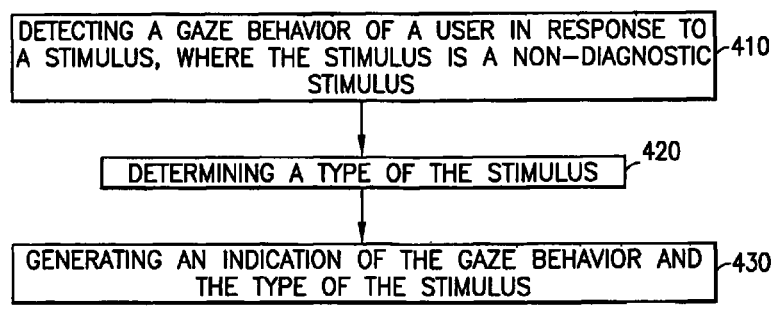
FIG. 4 is a logic flow diagram that illustrates the operation of an exemplary method, and a result of execution of computer program instructions embodied on a computer readable memory, in accordance with various exemplary embodiments.

FIG. 4 is a logic flow diagram that illustrates the operation of a method, and a result of execution of computer program instructions, in accordance with exemplary embodiments. In accordance with these exemplary embodiments a method performs, at Block 410, a step of detecting a gaze behavior of a user in response to a stimulus. The stimulus is a non-diagnostic stimulus. A step of determining a type of the stimulus is performed by the method at Block 420. The method performs, at Block 430, a step of generating an indication of the gaze behavior and the type of the stimulus.

The various blocks shown in FIG. 4 may be viewed as method steps, and/or as operations that result from operation of computer program code, and/or as a plurality of coupled logic circuit elements constructed to carry out the associated function(s).

An exemplary embodiment provides a method to track a user's gaze for medical diagnostics. The method includes detecting (such as by a processor) a gaze behavior of a user in response to a stimulus. The stimulus is a non-diagnostic stimulus. The method also includes determining (such as by a processor) a type of the stimulus and generating (such as by a processor) an indication of the gaze behavior and the type of the stimulus.

In a further exemplary embodiment of the method above, the method also includes determining a gaze pattern based on a plurality of gaze behaviors and associated types of stimuli. The plurality of gaze behaviors and associated types of stimuli include the gaze behavior and the type of stimulus.

In another exemplary embodiment of any one of the methods above, the method also includes determining whether the gaze behavior to the type of stimulus deviates from a gaze pattern.

In a further exemplary embodiment of any one of the methods above, the method also includes, in response determining that the gaze behavior to the type of stimulus matches a known behavior, generating an alert.

In another exemplary embodiment of any one of the methods above, determining the type of the stimulus includes receiving an image from a camera facing in the direction of the gaze and determining the type of the stimulus in the image. Alternatively, determining the type of the stimulus includes determining a type of an image shown on a display. The display may be a NED device.

In a further exemplary embodiment of any one of the methods above, the method also includes storing the indication of the gaze behavior and the type of stimulus.

In another exemplary embodiment of any one of the methods above, the stimulus is a real world stimulus. A real world stimulus includes physical objects (such as people, text, etc.) as well as computer generated images encountered in non-diagnostic settings (such as when operating a word processor, gaming application, web browser, etc.).

A further exemplary embodiment provides an apparatus to track a user's gaze for medical diagnostics. The apparatus includes at least one processor and at least one memory storing computer program code. The at least one memory and the computer program code are configured to, with the at least one processor, cause the apparatus to perform actions. The actions include detecting a gaze behavior of a user in response to a stimulus. The stimulus is a non-diagnostic stimulus. The actions also include determining a type of the stimulus and generating an indication of the gaze behavior and the type of the stimulus.

In another exemplary embodiment of the apparatus above, the actions also include determining a gaze pattern based on a plurality of gaze behaviors and associated types of stimuli. The plurality of gaze behaviors and associated types of stimuli include the gaze behavior and the type of stimulus.

In a further exemplary embodiment of any one of the apparatus above, the actions also include determining whether the gaze behavior to the type of stimulus deviates from a gaze pattern.

In another exemplary embodiment of any one of the apparatus above, the actions also include, in response determining that the gaze behavior to the type of stimulus matches a known behavior, generating an alert.

In a further exemplary embodiment of any one of the apparatus above, determining the type of the stimulus includes receiving an image from a camera facing in the direction of the gaze and determining the type of the stimulus in the image. Alternatively, determining the type of the stimulus includes determining a type of an image shown on a display. The display may be a NED device.

In another exemplary embodiment of any one of the apparatus above, the actions also include storing the indication of the gaze behavior and the type of stimulus.

In a further exemplary embodiment of any one of the apparatus above, the stimulus is a real world stimulus.

In another exemplary embodiment of any one of the apparatus above, the apparatus is embodied in a mobile device.

In a further exemplary embodiment of any one of the apparatus above, the apparatus is embodied in an integrated circuit.

Another exemplary embodiment provides a computer readable medium to track a user's gaze for medical diagnostics. The computer readable medium is tangibly encoded with a computer program executable by a processor to perform actions. The actions include detecting a gaze behavior of a user in response to a stimulus. The stimulus is a non-diagnostic stimulus. The actions also include determining a type of the stimulus and generating an indication of the gaze behavior and the type of the stimulus.

In a further exemplary embodiment of the computer readable medium above, the actions also include determining a gaze pattern based on a plurality of gaze behaviors and associated types of stimuli. The plurality of gaze behaviors and associated types of stimuli include the gaze behavior and the type of stimulus.

In another exemplary embodiment of any one of the computer readable media above, the actions also include determining whether the gaze behavior to the type of stimulus deviates from a gaze pattern.

In a further exemplary embodiment of any one of the computer readable media above, the actions also include, in response determining that the gaze behavior to the type of stimulus matches a known behavior, generating an alert.

In another exemplary embodiment of any one of the computer readable media above, determining the type of the stimulus includes receiving an image from a camera facing in the direction of the gaze and determining the type of the stimulus in the image. Alternatively, determining the type of the stimulus includes determining a type of an image shown on a display. The display may be a NED device.

In a further exemplary embodiment of any one of the computer readable media above, the actions also include storing the indication of the gaze behavior and the type of stimulus.

In another exemplary embodiment of any one of the computer readable media above, the stimulus is a real world stimulus.

In a further exemplary embodiment of any one of the computer readable media above, the computer readable medium is a non-transitory computer readable medium (e.g., CD-ROM, RAM, flash memory, etc.).

In another exemplary embodiment of any one of the computer readable media above, the computer readable medium is a storage medium.

A further exemplary embodiment provides an apparatus to track a user's gaze for medical diagnostics. The apparatus includes means for detecting (such as a processor) a gaze behavior of a user in response to a stimulus. The stimulus is a non-diagnostic stimulus. The apparatus also includes means for determining (such as a processor) a type of the stimulus and means for generating (such as a processor) an indication of the gaze behavior and the type of the stimulus.

In another exemplary embodiment of the apparatus above, the apparatus also includes means for determining a gaze pattern based on a plurality of gaze behaviors and associated types of stimuli. The plurality of gaze behaviors and associated types of stimuli include the gaze behavior and the type of stimulus.

In a further exemplary embodiment of any one of the apparatus above, the apparatus also includes means for determining whether the gaze behavior to the type of stimulus deviates from a gaze pattern.

In another exemplary embodiment of any one of the apparatus above, the apparatus also includes means for generating an alert in response determining that the gaze behavior to the type of stimulus matches a known behavior.

In a further exemplary embodiment of any one of the apparatus above, the determining means includes means for receiving an image from a camera facing in the direction of the gaze and means for determining the type of the stimulus in the image. Alternatively, the determining means includes means for determining a type of an image shown on a display. The display may be a NED device.

In another exemplary embodiment of any one of the apparatus above, the apparatus also includes means for storing the indication of the gaze behavior and the type of stimulus.

In a further exemplary embodiment of any one of the apparatus above, the stimulus is a real world stimulus.

In general, the various exemplary embodiments may be implemented in hardware or special purpose circuits, software, logic or any combination thereof. For example, some aspects may be implemented in hardware, while other aspects may be implemented in firmware or software which may be executed by a controller, microprocessor or other computing device, although not limited thereto. While various aspects of the exemplary embodiments may be illustrated and described as block diagrams, flow charts, or using some other pictorial representation, it is well understood that these blocks, apparatus, systems, techniques or methods described herein may be implemented in, as nonlimiting examples, hardware, software, firmware, special purpose circuits or logic, general purpose hardware or controller or other computing devices, or some combination thereof.

It should thus be appreciated that at least some aspects of the exemplary embodiments may be practiced in various components such as integrated circuit chips and modules, and that the exemplary embodiments may be realized in an apparatus that is embodied as an integrated circuit. The integrated circuit, or circuits, may comprise circuitry (as well as possibly firmware) for embodying at least one or more of a data processor or data processors that are configurable so as to operate in accordance with the exemplary embodiments.

Various modifications and adaptations to the foregoing exemplary embodiments may become apparent to those skilled in the relevant arts in view of the foregoing description, when read in conjunction with the accompanying drawings. However, any and all modifications will still fall within the scope of the non-limiting and exemplary embodiments.

For example, while the exemplary embodiments have been described above in the context of a NED system, it should be appreciated that the exemplary embodiments are not limited for use with only this one particular type of gaze tracking system, and that they may be used to advantage in other gaze tracking systems.

Various exemplary embodiments aid clinicians and other potential users in diagnosing medical conditions whose symptoms are expressed through eye movements, such as when presented with stimuli. While previous solutions involve large, bulky equipment, newer gaze tracking devices offer portable devices which may be used outside the laboratory setting. With a lightweight gaze tracking solution (such as one that is incorporated in a computer that is used daily), data collection for medical diagnosis can be performed without added work. In addition, no distracting unnatural stimuli are necessary and the system can be used to monitor the user during everyday use.

Extending the ability to monitor medical conditions with lightweight gaze tracking solutions allows medical personal to develop a more detailed understanding of any gaze related issues. While a greater amount of data is available, this is only one advantage. Patients reacting to real world stimuli may generate more 'accurate' results than in the exam room setting. Additionally, momentary gaze characteristics may be detected which may not necessarily occur when the patient is being tested. Furthermore, if the patient's gaze demonstrates a potential problem, an alert may be provided to the patient and/or medical personal.

For example, the gaze tracking device may determine patterns of the user's gaze movements automatically using a plurality of gaze tracking measurements and/or by having patterns provided to the device (such as from a medical professional setting up the gaze tracking device). Once the user's gaze movement patterns are identified, deviations from those patterns can be detected. The presence and/or type of deviation can be recorded. Additionally, an alert of the presence and/or type of deviation may be generated. Features as described herein may utilize gaze tracking (such as visual monitoring of eye movement and eye characteristics) on a near eye display to measure eye movement while the user is performing non-diagnostic activities with the display (such as every-day use of the device) and comparing the eye movement with supplemental information (such as a predetermined gaze pattern for example) to determine if there is a possible medical problem, or what is being viewed during symptoms of a medical problem exhibited by a person's eye(s), or what the person is doing or has been doing during symptoms of a medical problem exhibited by a person's eye(s). The supplemental information may be related to information this displayed on the near-eye display, or to information that is viewed through the near-eye display (pass-through information). The supplemental information may be historical information which may be gathered by the device/apparatus over a period of time, and stored in a local or remote repository. Information may be recorded and stored including information relating to gaze behavior occurrence of when a problem is detected. Any information recorded by the device/apparatus may later be reviewed by a doctor.

It should be noted that the terms "connected," "coupled," or any variant thereof, mean any connection or coupling, either direct or indirect, between two or more elements, and may encompass the presence of one or more intermediate elements between two elements that are "connected" or "coupled" together. The coupling or connection between the elements can be physical, logical, or a combination thereof. As employed herein two elements may be considered to be "connected" or "coupled" together by the use of one or more wires, cables and/or printed electrical connections, as well as by the use of electromagnetic energy, such as electromagnetic energy having wavelengths in the radio frequency region, the microwave region and the optical (both visible and invisible) region, as several non-limiting and non-exhaustive examples.

Furthermore, some of the features of the various non-limiting and exemplary embodiments may be used to advantage without the corresponding use of other features. As such, the foregoing description should be considered as merely illustrative of the principles, teachings and exemplary embodiments, and not in limitation thereof.

What is claimed is:

1. A method comprising:
    detecting a gaze behavior of a user in response to a stimulus, where the stimulus is a non-diagnostic stimulus that is a visual stimulus that is not specifically created or generated for a diagnostic testing machine or method;
    determining a type of the non-diagnostic visual stimulus by using a camera to image a scene being viewed by the user and by using a processor-implemented object recognition technique to identify an object or objects in the imaged scene to which the gaze of the user is directed;
    assigning the identified object or objects to a particular non-diagnostic visual stimulus classification and type of non-diagnostic visual stimulus;
    associating the detected gaze behavior with the identified object or objects; and
    generating an indication of the gaze behavior and the determined type of the non-diagnostic visual stimulus.

2. The method of claim 1, further comprising determining a gaze pattern based on a plurality of gaze behaviors and associated types of non-diagnostic visual stimuli, where the plurality of gaze behaviors and associated types of non-diagnostic visual stimuli comprise the gaze behavior and the type of non-diagnostic visual stimulus.

3. The method of claim 1, further comprising determining whether the gaze behavior to the type of non-diagnostic visual stimulus deviates from a gaze pattern.

4. The method of claim 1, further comprising, in response determining that the gaze behavior to the type of non-diagnostic visual stimulus matches a known behavior, generating an alert.

5. The method of claim 1, where determining the type of the non-diagnostic visual stimulus comprises using at least one of optical character recognition, template matching, weak classifier cascades, bag of features, edge-matching, and histogram matching, and further comprising classifying an identified object in the scene as to a type of non-diagnostic visual stimulus.

6. The method of claim 1, where determining the type of the non-diagnostic visual stimulus further comprises determining a type of an image shown on a display.

7. The method of claim 1, where determining the type of the non-diagnostic visual stimulus further comprises determining a type of an image shown on a display, and where the display is a near eye display device.

8. The method of claim 1, further comprising storing the indication of the gaze behavior and the type of non-diagnostic visual stimulus.

9. The method of claim 1, where the non-diagnostic visual stimulus that is detected by the method is a real world non-diagnostic visual stimulus.

10. An apparatus, comprising:
at least one processor;
a gaze tracker having an output coupled to the processor;
at least one camera having an output coupled to the processor; and
at least one memory including computer program code, the at least one memory and the computer program code configured to, with the at least one processor, control the apparatus to perform, as a result of execution of the computer program code by the at least one processor, operations that comprise:
detect based at least in part on an output of the gaze tracker a gaze behavior of a user in response to a stimulus, where the stimulus is a non-diagnostic stimulus that is a visual stimulus that is not specifically created or generated for a diagnostic testing machine or method;
determine using the at least one camera and the at least one processor a type of the non-diagnostic visual stimulus by using the at least one camera to image a scene being viewed by the user and by using an object recognition technique executed by the at least one processor to identify an object or objects in the imaged scene to which the gaze of the user is directed;
assign using the at least one processor the identified object or objects to a particular non-diagnostic visual stimulus classification and type of non-diagnostic visual stimulus;
associate the detected gaze behavior with the identified object or objects; and
generate and store in the at least one memory an indication of the gaze behavior and the determined type of the non-diagnostic visual stimulus.

11. The apparatus of claim 10, where the operations that result from the execution of the computer program code by the at least one processor further comprise:
determine a gaze pattern based on a plurality of gaze behaviors and associated types of non-diagnostic visual stimuli, where the plurality of gaze behaviors and associated types of non-diagnostic visual stimuli comprise the gaze behavior and the type of non-diagnostic visual stimulus.

12. The apparatus of claim 10, where the operations that result from the execution of the computer program code by the at least one processor further comprise:
generate an alert in response determining that the gaze behavior to the type of non-diagnostic visual stimulus matches a known gaze behavior.

13. The apparatus of claim 10, where the operations that result from the execution of the computer program code by the at least one processor further comprise:
when determining the type of the non-diagnostic visual stimulus, control the apparatus to receive an image from the at least one camera that is disposed to be facing in the direction of the gaze; and
determine the type of the non-diagnostic visual stimulus in the image in accordance with least one of optical character recognition, template matching, weak classifier cascades, bag of features, edge-matching, and histogram matching.

14. The apparatus of claim 10, where the operations that result from the execution of the computer program code by the at least one processor further comprise:
when determining the type of the non-diagnostic visual stimulus, control the apparatus to determine a type of an image shown on a display.

15. A computer readable medium tangibly encoded with a computer program executable by a processor to perform actions comprising:
detecting a gaze behavior of a user in response to a stimulus, where the stimulus is a non-diagnostic stimulus that is a visual stimulus that is not specifically created or generated for a diagnostic testing machine or method;
determining a type of the non-diagnostic visual stimulus by using a camera to image a scene being viewed by the user and by using an object recognition technique to identify an object or objects in the imaged scene to which the gaze of the user is directed;
assigning the identified object or objects to a particular non-diagnostic visual stimulus classification and type of non-diagnostic visual stimulus;
associating the detected gaze behavior with the identified object or objects; and
generating an indication of the gaze behavior and the determined type of the non-diagnostic visual stimulus.

16. The computer readable medium of claim 15, the actions further comprising determining a gaze pattern based on a plurality of gaze behaviors and associated types of non-diagnostic visual stimuli, where the plurality of gaze behaviors and associated types of non-diagnostic visual stimuli comprise the gaze behavior and the type of non-diagnostic visual stimulus.

17. The computer readable medium of claim 15, the actions further comprising, in response determining that the gaze behavior to the type of non-diagnostic visual stimulus matches a known behavior, generating an alert.

18. The computer readable medium of claim 15, where determining the type of the non-diagnostic visual stimulus comprises using at least one of optical character recognition, template matching, weak classifier cascades, bag of features, edge-matching, and histogram matching, and further comprising classifying an identified object or objects in the scene as to a type of non-diagnostic visual stimulus.

19. A method, comprising:
in response to a user wearing a headset that comprises a gaze tracker that faces in a direction of the user's eyes, a transparent lens through which the user can view a scene and a forward facing camera configured to image the scene viewed by the user;

identifying, using a processor-implemented object recognition technique, an object or objects in the imaged scene to which the gaze of the user is currently being directed;

classifying an identified object or objects in the scene as to being a determined one of a plurality of types of non-diagnostic visual stimulus, where a non-diagnostic visual stimulus is a visual stimulus that is not specifically created or generated for a diagnostic testing machine or method;

determining a gaze pattern of the user in response to the non-diagnostic visual stimulus resulting from the object or objects in the scene being viewed by the user;

associating the determined gaze pattern with the identified object or objects; and comparing the determined gaze pattern to historically determined gaze patterns of the user that correspond to a same determined type of non-diagnostic visual stimulus.

20. The method as in claim 19, where identifying the object or objects in the images scene comprises using at least one of processor-executed optical character recognition, template matching, weak classifier cascades, bag of features, edge-matching, and histogram matching.

* * * * *